United States Patent [19]

Meek et al.

[11] Plant 4,959

[45] Nov. 30, 1982

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 184,402

[22] Filed: Sep. 4, 1980

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Charlie having flat capitulum form; daisy capitulum type; medium yellow ray floret color with minimum color oxidation; yellow-green (immature) to yellow (mature) disc floret color; diameter across face of capitulum ranging from 70 to 90 mm. at maturity; uniform nine week photoperiodic flowering response to short days; tall plant height when grown as a single stem cut spray; medium peduncle length; and minimum pollen production.

1 Drawing Figure

The present invention comprises a new and distinct cultivar of *Chrysanthemum morifolium,* Ramat., hereinafter referred to by the cultivar name Charlie.

Charlie is an induced mutation of Charisma, disclosed in U.S. Plant Pat. No. 4,561.

Charlie was discovered and selected as one flowering plant within a flowering block of the parental seedling by William E. Duffett on July 31, 1979 in a controlled environment in Salinas, Calif. Plants within the flowering block were derived from stock plants which had been irradiated as unrooted cuttings with an x-ray source of 2600 R units.

The first act of asexual reproduction of Charlie was accomplished when vegetative cuttings were taken from the initial selection in January, 1980 in a controlled environment in Salinas, Calif. by a technician working under formulations established and supervised by Jack M. Meek. Continued asexual reproduction by vegetative cuttings for evaluative tests in flowering and stock programs in conjunction with horticultural examination of selected plants initiated July 31, 1979 has demonstrated that the combination of characteristics as herein disclosed for Charlie are firmly fixed and are retained through successive generations of asexual reproduction.

Charlie has not been observed under all possible environmental conditions. The phenotype may vary significantly with variations in environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristics of Charlie which in combination distinguish this chrysanthemum as a new and distinct cultivar:

(1) Flat capitulum form,
(2) Daisy capitulum type,
(3) Medium yellow ray floret color with minimum color oxidation,
(4) Yellow-green (immature) to yellow (mature) disc floret color,
(5) Diameter across face of capitulum ranging from 70 to 90 mm. at maturity, (6) Uniform nine week photoperiodic flowering response to short days,
(7) Tall plant height (attaining a height as a flowered plant of 70 to 75 cm. from a rooted cutting planted to short days for April through November flowerings),
(8) Medium peduncle length, and
(9) Minimal pollen production.

Of the many commercial cultivars known to the present inventors, the most similar in comparison to Charlie are Charisma and Florida Marble, disclosed in U.S. Plant Pat. No. 3,288. Reference is made to attached Chart A which compares certain characteristics of Charlie to those same chracteristics of Charisma and Florida Marble.

In comparison to Charisma, Charlie has different ray floret color. The capitulum form, capitulum type, diameter across face of capitulum, plant height, flowering response period and peduncle length of Charisma are similar to those same characteristics of Charlie.

In comparison to Florida Marble, Charlie has slower ray floret color oxidation, larger diameter across face of capitulum, taller plant height, and shorter peduncle length. The ray floret color, capitulum form, capitulum type, and flowering response period of Florida Marble are similar to those same characteristics of Charlie.

The accompanying drawings show typical inflorescence and foliage characteristics of Charlie. Sheet 1 is a perspective view showing the inflorescence of Charlie. The color of the ray and disc florescence is as accurate as possible with color renditions of this type.

In the following description, color references are made to A Limit Color Cascade by the Munsell Company, 1972 edition. The color values were determined between 1:00 and 1:30 P.M. on July 17, 1980 under 100 foot-candle light intensity at Salinas, Calif.

Classification:

*Botanical.*—*Chrysanthemum morifolium,* Ramat., cv Charlie.

*Commercial.*—Cut daisy spray.

I. Inflorescence:

A. *Capitulum.*—Form; Flat. Type: Daisy. Diameter across face: 70 to 90 mm.

B. *Corolla of ray florets.*—General tonality from a distance of 3 meters: Yellow - 25-5 to 26-5. Color (abaxial): Approximately 25-5 to 25-4. Color (adaxial): Approximately 26-3 to 26-2.

C. *Corolla of disc florets.*—Color (immature): 23-10 to 23-9. Color (mature): 27-6.

D. *Reproductive organs.*—Androecium: Present disc florets only; scant to few; scant pollen. Gynoecium: Present both ray and disc florets.

II. Plant:

A. *General appearance.*—Height: Tall, 75 to 85 cm. Branching pattern: Semi-upright.

B. *Foliage.*—Color (abaxial): Approximately 21-15. Color (adaxial): Approximately 21-15 overlaid with white. Shape: Deeply lobed and coarsely serrated.

CHART A

COMPARISON OF CHARLIE, CHARISMA AND FLORIDA MARBLE

| CULTIVAR | RAY FLORET COLOR | CAPITULUM FORM & TYPE | DIAMETER ACROSS FACE OF CAPITULUM |
|---|---|---|---|
| CHARLIE | Medium Yellow with minimum color oxidation | Flat Daisy | 70 to 90 mm. |
| CHARISMA | Dark Lavender Pink | Flat Daisy | 70 to 90 mm. |
| FLORIDA MARBLE | Medium Yellow with rapid oxidation | Flat Daisy | 60 to 85 mm. |

CHART A-continued

COMPARISON OF CHARLIE, CHARISMA AND FLORIDA MARBLE

| CULTIVAR | PLANT HEIGHT | FLOWERING RESPONSE PERIOD | PEDUNCLE LENGTH |
|---|---|---|---|
| CHARLIE | Tall, 70 to 75 cm. | 9 week | Medium, 85 to 110 mm. |
| CHARISMA | Tall, 70 to 75 cm. | 9 week | Medium, 85 to 110 mm. |
| FLORIDA MARBLE | Medium, 60 to 65 cm. | 9 week | Long, 150 to 200 mm. |

COMPARISONS MADE OF PLANTS GROWN AS SINGLE STEM CUT SPRAYS WITH NO LONG DAYS IN SALINAS, CALIFORNIA

We claim:

1. A new and distinct cultivar *Chrysanthemum morifolium,* Ramat., plant known by the cultivar name Charlie, as described and illustrated, and particularly characterized as to uniqueness by the combined characteristics of flat capitulum form; daisy capitulum type, medium yellow ray floret color with minimum color oxidation; yellow green (immature) to yellow (mature) disc floret color; diameter across face of capitulum ranging from 70 to 90 mm. at maturity; uniform nine week photoperiodic flowering response to short days; tall plant height; medium peduncle length, and minimal pollen production.

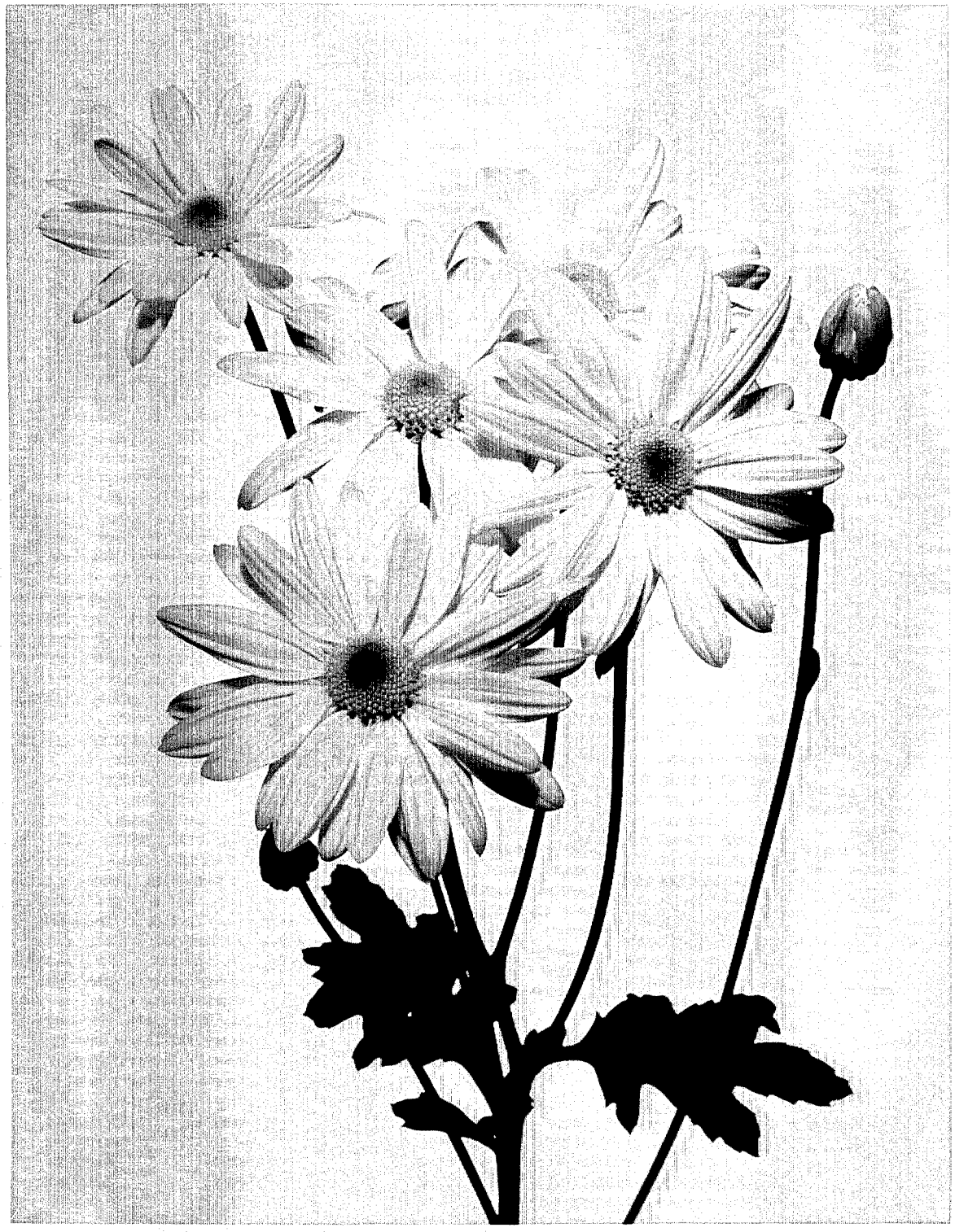

* * * * *